US00PP23819P2

(12) United States Plant Patent
Degenhardt

(10) Patent No.: US PP23,819 P2
(45) Date of Patent: Aug. 6, 2013

(54) ***ECHINACEA* PLANT NAMED 'RED BARON'**

(50) Latin Name: *Echinacea purpurea*
Varietal Denomination: Red Baron

(75) Inventor: Dick Degenhardt, Boskoop (NL)

(73) Assignee: Compass Plants BV, Hillegom (NL)

( * ) Notice: Subject to any disclaimer, the term of this patent is extended or adjusted under 35 U.S.C. 154(b) by 0 days.

(21) Appl. No.: 13/374,567

(22) Filed: Dec. 31, 2011

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Kent L Bell
(74) *Attorney, Agent, or Firm* — C. A. Whealy

(57) ABSTRACT

A new and distinct cultivar of *Echinacea* plant named 'Red Baron', characterized by its upright and columnar plant habit; moderately vigorous to vigorous growth habit; strong flowering stems; freely flowering habit; long flowering period; large inflorescences with grey purple-colored ray florets, dark grey purple-colored disc florets and red-colored receptacle spines; ray florets arranged in a single whorl at the base of the receptacle and randomly towards the receptacle apex; and good garden performance.

3 Drawing Sheets

Botanical designation: *Echinacea purpurea.*
Cultivar denomination: 'RED BARON'.

BACKGROUND OF THE INVENTION

The present invention relates to a new and distinct cultivar of *Echinacea* plant, botanically known as *Echinacea purpurea*, and hereinafter referred to by the name 'Red Baron'.

The new *Echinacea* plant is a product of a planned breeding program conducted by the Inventor in Boskoop, The Netherlands. The objective of the breeding program is to develop new freely flowering *Echinacea* plants with unique inflorescence forms and attractive ray and disc floret coloration.

The new *Echinacea* plant originated from a cross-pollination conducted by the Inventor in 2001 in Boskoop, The Netherlands of two unnamed proprietary selections of *Echinacea purpurea*, not patented. The new *Echinacea* plant was discovered and selected by the Inventor as a single flowering plant from within the progeny of the stated cross-pollination grown in a controlled environment in Boskoop, The Netherlands in 2003.

Asexual reproduction of the new *Echinacea* plant by divisions in a controlled environment in Boskoop, The Netherlands since 2003 has shown that the unique features of this new *Echinacea* plant are stable and reproduced true to type in successive generations.

SUMMARY OF THE INVENTION

Plants of the new *Echinacea* have been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Red Baron'. These characteristics in combination distinguish 'Red Baron' as a new and distinct *Echinacea* plant:

1. Upright and columnar plant habit.
2. Moderately vigorous to vigorous growth habit.
3. Strong flowering stems.
4. Freely flowering habit.
5. Long flowering period.
6. Large inflorescences with grey purple-colored ray florets, dark grey purple-colored disc florets and red-colored receptacle spines; ray florets arranged in a single whorl at the base of the receptacle and randomly towards the receptacle apex.
7. Good garden performance.

Plants of the new *Echinacea* can be compared to plants of the parent selections. Plants of the new *Echinacea* differ from plants of the parent selections in the following characteristics:

1. Plants of the new *Echinacea* are shorter than plants of the parent selections.
2. Plants of the new *Echinacea* are more freely flowering than plants of the parent selections.
3. Plants of the new *Echinacea* and the parent selections differ in ray floret color as ray florets of plants of the parent selections are pink in color.

Plants of the new *Echinacea* can be compared to plants of *Echinacea purpurea* 'Doppelganger', not patented. In side-by-side comparisons conducted in Boskoop, The Netherlands, plants of the new *Echinacea* differed primarily from plants of 'Doppelganger' in the following characteristics:

1. Plants of the new *Echinacea* were shorter than plants of 'Doppelganger'.
2. Plants of the new *Echinacea* were more freely flowering than plants of 'Doppelganger'.
3. Plants of the new *Echinacea* had larger inflorescences than plants of 'Doppelganger'.
4. Plants of the new *Echinacea* and 'Doppelganger' differed in ray floret color as ray florets of plants of 'Doppelganger' were pink in color.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Red Baron' grown in a container.

The photograph on the second sheet is a close-up view of a typical inflorescence of 'Red Baron'.

The photograph on the third sheet is a close-up view of the upper surface of a typical leaf of 'Red Baron'.

DETAILED BOTANICAL DESCRIPTION

The aforementioned photographs and following observations and measurements describe plants grown during the late summer in an outdoor nursery in Hillegom, The Netherlands and under cultural practices which approximate those generally used in commercial *Echinacea* production. During the production of the plants, day temperatures ranged from 14° C. to 28° C. and night temperatures ranged from 8° C. to 16° C. Measurements and numerical values represent averages for typical flowering plants. Plants were two years old when the photographs and description were taken. In the following description, color references are made to The Royal Horticultural Society Colour Chart, 2007 Edition, except where general terms of ordinary dictionary significance are used.

Botanical classification: *Echinacea purpurea* 'Red Baron'.

Parentage:

*Female parent*.—Unnamed proprietary selection of *Echinacea purpurea*, not patented.

*Male parent*.—Unnamed proprietary selection of *Echinacea purpurea*, not patented.

Propagation:

*Type*.—By divisions.

*Time to initiate roots, summer*.—About three weeks at 20° C.

*Time to produce a rooted young plant, summer*.—About two months at 20° C.

*Root description*.—Fine, fibrous; black in color.

*Rooting habit*.—Freely branching; medium density.

Plant description:

*Plant form/growth habit*.—Herbaceous perennial; upright and columnar plant habit, narrow inverted triangle; freely basal branching habit with about ten branches developing per plant; moderately vigorous to vigorous growth habit.

*Plant height*.—About 91 cm.

*Plant diameter or spread*.—About 46 cm.

*Branches*.—Length: About 56.2 cm. Diameter: About 8 mm. Internode length: About 3.9 cm. Aspect: Erect to about 5° from vertical. Strength: Strong. Texture: Pubescent, strigose; rough. Color: Close to 144A.

Foliage description:

*Arrangement*.—Alternate, simple.

*Length*.—About 14.5 cm.

*Width*.—About 7.1 cm.

*Shape*.—Narrowly ovate.

*Apex*.—Narrowly acute.

*Base*.—Narrowly cuneate.

*Margin*.—Sparsely dentate; undulate.

*Texture, upper and lower surfaces*.—Pubescent, strigose; rough.

*Venation pattern*.—Pinnate.

*Color*.—Developing leaves, upper surface: Close to 137A. Developing leaves, lower surface: Close to 137C. Fully expanded leaves, upper surface: Close to 137A; venation, close to 145A. Fully expanded leaves, lower surface: Close to 137C and 147B; venation, close to 145A to 145B.

*Petioles, basal leaves*.—Length: About 7.1 cm. Diameter: About 3 mm. Texture, upper and lower surfaces: Pubescent, strigose. Color, upper surface: Close to 1437C strongly tinged with close to 187B. Color, lower surface: Close to 144B.

Inflorescence description:

*Appearance*.—Rotate inflorescence form with ray and disc florets arranged on a capitulum; inflorescences positioned upright above the foliar plane on upright strong peduncles.

*Flowering habit*.—Freely flowering habit with about seven inflorescences per branch; about 70 inflorescences developing per plant.

*Fragrance*.—Faint, acidic-sweet, pleasant.

*Time to flower*.—Plants begin flowering about three months after planting and in the garden, plants flower continuously from early July to the middle of September in The Netherlands.

*Inflorescence longevity*.—Inflorescences maintain good substance for about three weeks on the plant; inflorescences not persistent.

*Inflorescence bud*.—Height: About 1.7 cm. Diameter: About 2.5 cm. Shape: Flattened globular. Color: Close to 144C.

*Inflorescence size*.—Diameter: About 11.4 cm. Depth (height): About 7.2 cm. Disc diameter: About 3.8 cm. Receptacle height: About 2.1 cm. Receptacle diameter: About 1.3 cm. Receptacle color: Close to 155A.

*Ray florets, basal*.—Quantity and arrangement: About 30 in a single whorl at the base of the receptacle. Length: About 4.5 cm. Width: About 8 mm. Shape: Narrowly oblanceolate. Apex: Narrowly acute. Base: Cuneate. Margin: Entire. Texture, upper and lower surfaces: Smooth, glabrous; slightly longitudinally ridged. Aspect: Horizontal to slightly drooping, about 10° from horizontal. Color: When opening, upper surface: Close to 64B. When opening, lower surface: Close to 186B; towards the apex, tinged with close to 146D. Fully opened, upper surface: Close to 185C; color does not fade with development. Fully opened, lower surface: Close to 59B to 59C.

*Ray florets, apical*.—Quantity and arrangement: About 20 randomly arranged towards the apex of the receptacle. Length: About 3 cm. Width: About 6 mm. Shape: Oblanceolate. Apex: Acute. Base: Cuneate. Margin: Entire. Texture, upper and lower surfaces: Smooth, glabrous; slightly longitudinally ridged. Color: When opening, upper surface: Close to 64B. When opening, lower surface: Close to 186B; towards the apex, tinged with close to 146D. Fully opened, upper surface: Close to 185C; color does not fade with development. Fully opened, lower surface: Close to 59B to 59C.

*Disc florets*.—Length: About 9 mm. Diameter: About 1.5 mm. Shape: Tubular, apices acute. Number of disc florets per inflorescence: More than 500. Texture, upper and lower surfaces: Smooth, glabrous. Color, immature, inner and outer surfaces: Close to N186C. Color, mature, inner and outer surfaces: Close to N186C.

*Receptacle spines*.—Quantity: One per disc floret. Shape: Acicular. Apex: Acute. Base: Attenuate. Texture: Smooth, glabrous. Color: Apex: Close to 42B. Mid-section: Close to 144B. Base: Close to 157D.

*Involucral bracts*.—Quantity per inflorescence: About 75 arranged in about three whorls. Length: About 1 cm. Width: About 3 mm. Shape: Ovate. Apex: Acute. Base: Cuneate. Margin: Entire. Texture, upper surface: Smooth, glabrous. Texture, lower surface: Sparsely pubescent; margins, moderately pubescent. Color, upper surface: Close to 137B. Color, lower surface: Close to 137C.

*Peduncles*.—Length, terminal peduncle: About 22.7 cm. Length, fourth peduncle: About 18.9 cm. Length, seventh peduncle: About 19.2 cm. Diameter: About 6 mm. Strength: Strong. Aspect: Upright to 30° from stem axis. Texture: Pubescent, strigose. Color: Close to 144A to 144B.

*Reproductive organs*.—Androecium (present on ray and disc florets): Quantity per floret: About four. Filament length: About 2 mm. Filament color: Close to 147B. Anther shape: Oblong. Anther length: About 1 mm. Anther color: Close to 147B. Pollen amount: Scarce. Pollen color: Close to 8A. Gynoecium (present only on disc florets): Quantity per floret: One. Pistil length: About 6 mm. Stigma shape: Decurrent. Stigma color: Close to N186C. Style length: About 5 mm. Style color: Close to N186C. Ovary color: Close to 157D. Seeds and fruits: Seed and fruit development have not been observed on plants of the new *Echinacea*.

Disease & pest resistance: Plants of the new *Echinacea* have not been shown to be resistant to pathogens and pests common to *Echinacea*.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Red Baron' as illustrated and described.

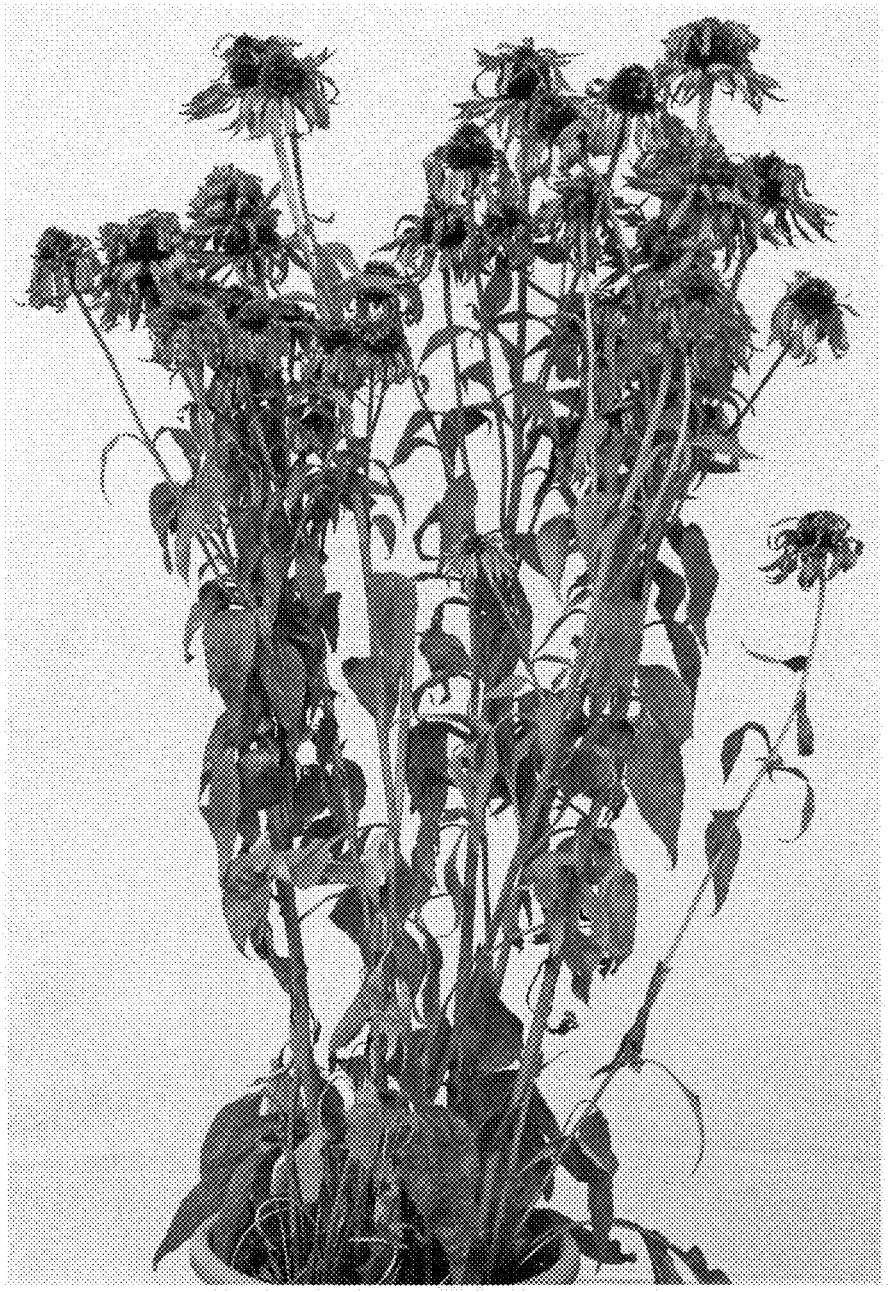

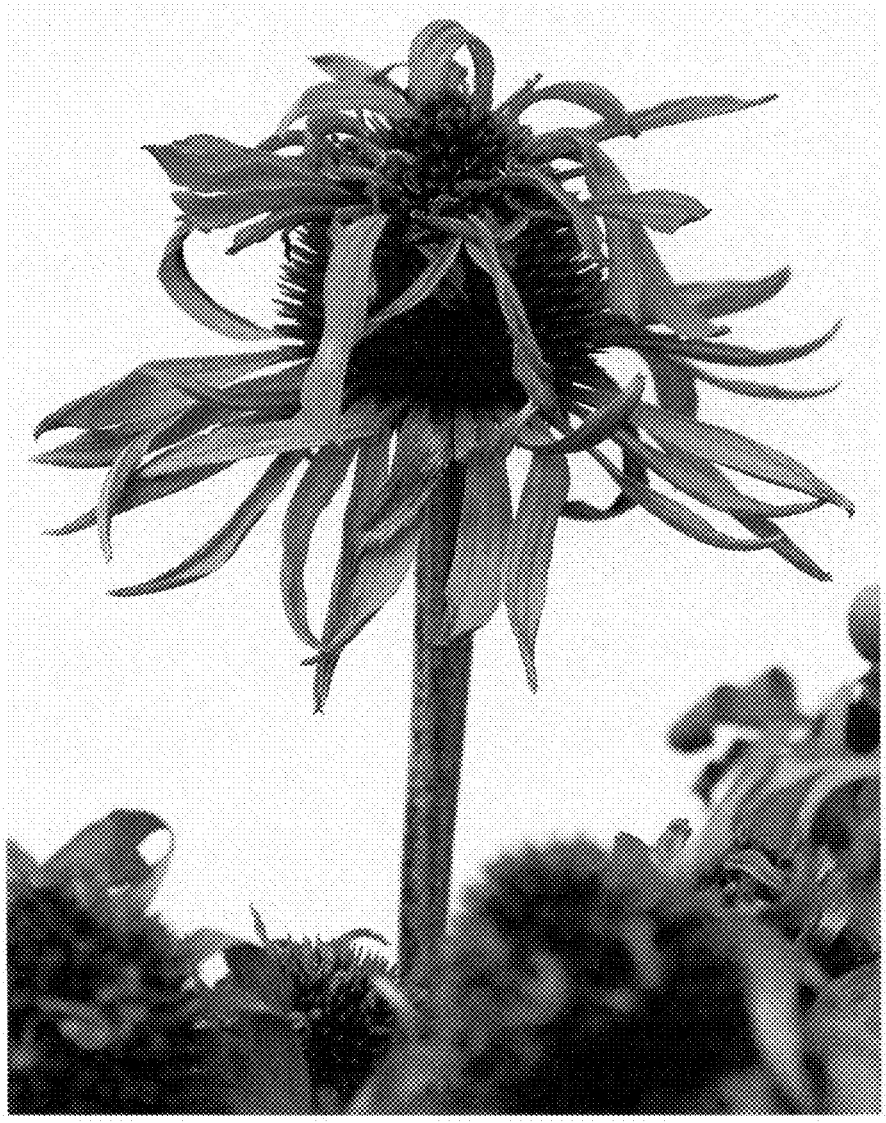

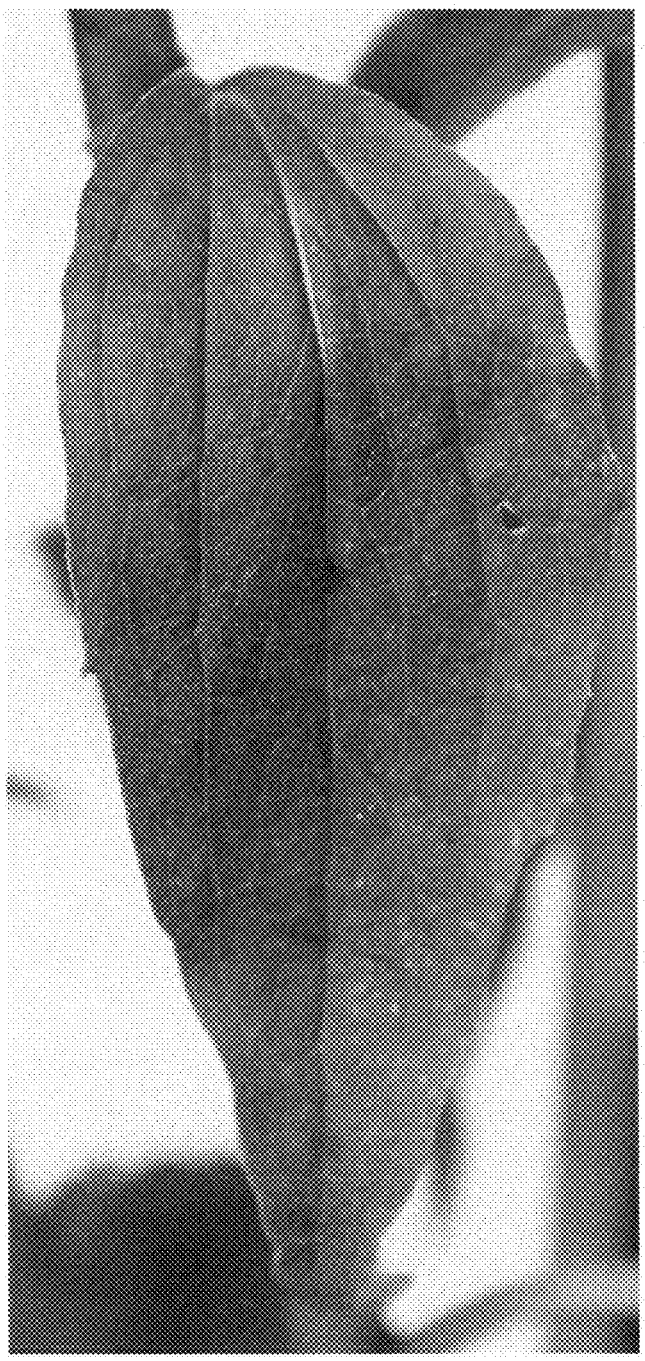

* * * * *